(12) United States Patent
Jang

(10) Patent No.: US 6,187,035 B1
(45) Date of Patent: *Feb. 13, 2001

(54) VASCULAR STENT

(76) Inventor: Yang-Soo Jang, Department of Cardiology, Severance Hospital, College of Medicine, Yonsei University, 134 Shinchon-Dong, Seodaemoon-Ku, Seoul 120-140 (KR)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/118,133

(22) Filed: Jul. 16, 1998

(30) Foreign Application Priority Data

Jul. 16, 1997 (KR) .................................. 97-33064

(51) Int. Cl.$^7$ ........................................ A61F 2/06
(52) U.S. Cl. ............................................ 623/1.15
(58) Field of Search ........................ 623/1, 12, 1.15, 623/1.16, 1.28

(56) References Cited

U.S. PATENT DOCUMENTS

| | | | |
|---|---|---|---|
| 5,607,442 | * | 3/1997 | Fischell et al. ........................ 623/1 |
| 5,755,771 | * | 5/1998 | Penn et al. ............................ 623/1 |
| 5,776,161 | * | 7/1998 | Globermann ........................... 623/1 |
| 5,776,181 | * | 7/1998 | Lee et al. .............................. 623/1 |

* cited by examiner

Primary Examiner—V. Milliw
Assistant Examiner—Suzette J. Jackson
(74) Attorney, Agent, or Firm—Knobbe Martens Olson & Bear, LLP

(57) ABSTRACT

The present invention relates to a vascular stent comprising wide vertical branches and narrow horizontal branches having wave-form projections, which has a vertically denser distribution. The vascular stent of the present invention comprises stainless steel-based vertical branches and horizontal branches having wave-form projections. The widths of the vertical branch and horizontal branch range 0.09 to 0.12 mm and 0.05 to 0.09 mm, respectively, while each thickness of those are identical to each other and range 0.08 to 0.12 mm. The vascular stent of the invention provides so superior flexibility as to afford excellent adaptability to the anatomy of the vessel. Moreover, the dense distribution of the branches improves strength of stability of the vascular stent, which allows the stent to sufficiently expand against high recoiling force. Implantation of the vascular stent to patients with coronary artery obrustructive disease (CAOD) can restore the constricted blood vessels to the original state, which normalizes the blood flow rate, and further, decreases the restenosis rate as well.

3 Claims, 5 Drawing Sheets

VASCULAR STENT

FIELD OF THE INVENTION

The present invention relates to a vascular stent, more specifically, to a vascular stent comprising wide vertical branches and narrow horizontal branches having wave-form projections, which has a vertically denser distribution.

BACKGROUND OF THE INVENTION

In general, the patients suffering from coronary artery obstructive disease ("CAOD"), accompany stenosis of coronary arteries or peripheral blood vessels caused by atheromatous plaques, which may result in decrease in blood flow rate, angina or even sudden death.

Treatment for the patients with CAOD includes the following methods: First, bypass surgery which aims to artificially maintain the blood flow via graft vessel has been introduced in the art. However, it accompanies severe pain at incision site and fear of the patient. Secondly, balloon catheter-using method has been suggested, which comprises a step of inserting a fine balloon catheter into narrowed blood vessel, fixing it at the constricted region and expanding the balloon to broaden the constricted region. Although this method solved the shortcomings of angioplasty to some extent, a problem still remains unsolved that restenosis rate is over 70%. Thirdly, a meshed metallic stent-using method, which comprises a step of inserting the meshed stainless-steel stent into a constricted blood vessel to expand the blood vessel to the normal width and recover normal flow rate of blood. This method slightly decreased restenosis which was observed in the said balloon catheter method, however, the said limitations of the conventional methods, e.g., pain and high restenosis rate, remained unsolved. Moreover, poor flexibility of the metallic stent raised a new problem that it is very difficult to apply the stent to a curved vessel.

SUMMARY OF THE INVENTION

In accordance with the present invention, a novel vascular stent is fabricated, which has wide vertical and narrow horizontal branches whose structures are able to be pressed to thinner profile to afford good adaptability to the anatomy of vessel. The vascular stent of the invention aims to decrease restenosis rate and provides superior flexibility to allow stenting in a bent of blood vessel. In addition, distribution of the branches vertically denser than conventional stents enables the stent to sufficiently extend against high recoiling pressure.

A primary object of the present invention is, therefore, to provide a vascular stent which comprises wide vertical branches and narrow horizontal branches having wave-form projections, which allows the thinner profile and maximal flexibility of the stent.

BRIEF DESCRIPTION OF THE DRAWINGS

The above and the other objects and features of the present invention will become apparent from the following descriptions given in conjunction with the accompanying drawings, in which.

DETAILED DESCRIPTION OF THE INVENTION

The vascular stent of the present invention comprises stainless steel-based vertical branches and horizontal branches having wave-form projections. The widths of the vertical branch and horizontal branch range 0.09 to 0.12 mm and 0.05 to 0.09 mm, respectively, while each thickness of those are identical to each other and range 0.08 to 0.12 mm.

Figure 1:
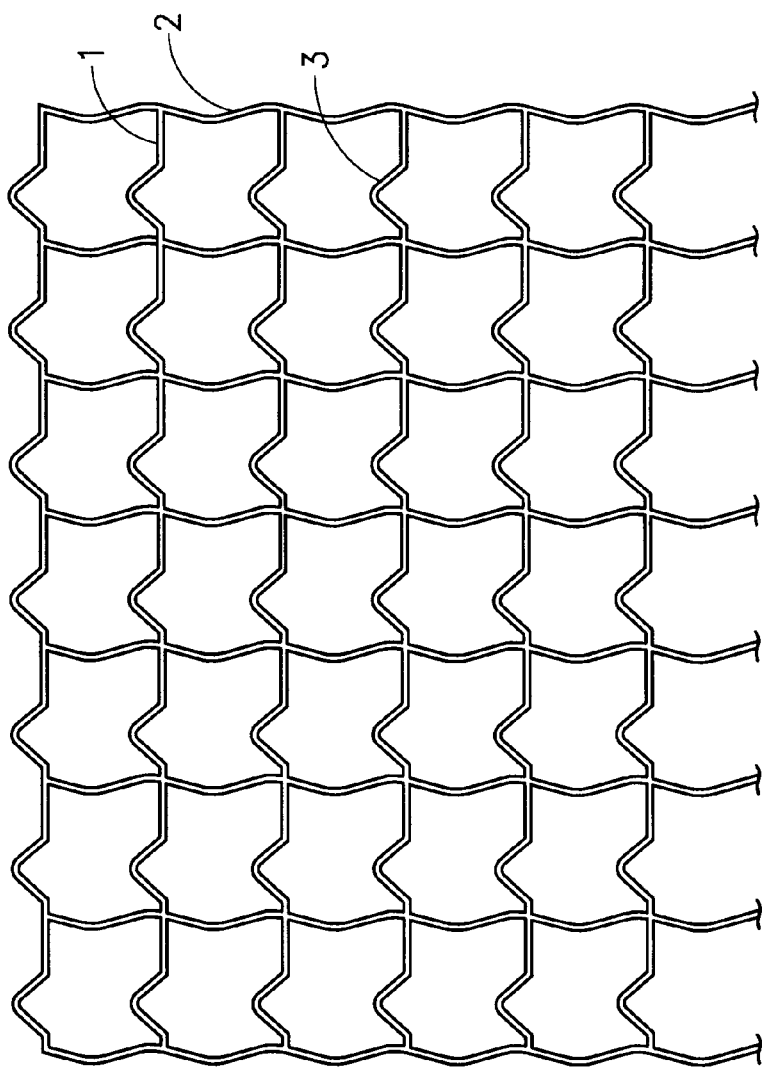
FIG. 1 is a development diagram depicting a vascular stent of the present invention.

FIG. 1 is a development figure of the vascular stent which comprises horizontal (1) and vertical branches (2) linked to each other. Each of the horizontal branch (1) possesses a wave-form projection (3) whose height is 0.3 to 0.8 mm, which endows the stent with excellent flexibility to adapt the stent to the anatomy of vessel. Further, the horizontal branch (1) has a width of 0.05 to 0.09 mm and a thickness of 0.08 to 0.12 mm, while the vertical branch (2) has a width of 0.09 to 0.12 mm and a thickness same to that of the horizontal branch (1). Intervention of the vascular stent of the invention into a narrowed blood vessel may successfully prevent restenosis since the thickness of the branches, i.e., a range of 0.08 to 0.12 mm, is thin enough to allow smooth blood flow, which, in turn, prevents thrombogenesis. In addition, difference in width between horizontal branches (1) and vertical branches (2) as mentioned above, improved flexibility of the vascular stent in a cooperative manner together with said wave-form projections, which guarantees excellent adaptation of the vascular stent to the anatomy of the vessel.

The vascular stent of the present invention is preferably fabricated by cutting a stainless steel tube whose diameter ranges 1.4 to 2.2 mm and trimming it well by the aid of laser beam, though the material of the stent and cutting technique may be varied by the conventionally skilled in the art. In the course of manufacturing the vascular stent, the diameter and length of the stent should fall in a range of 1.0 to 5.75 mm and 9 to 60 mm, respectively, while they depend on those of blood vessel in which the stent is inserted. Preferably, all of the branches are closely distributed for the sufficient expansion of the stent against high recoiling force. Thus, space between each horizontal branches (1) should range 1.0 to 3.0 mm and space between each vertical branches (2) should range 1.5 to 4.5 mm.

Figure 2:
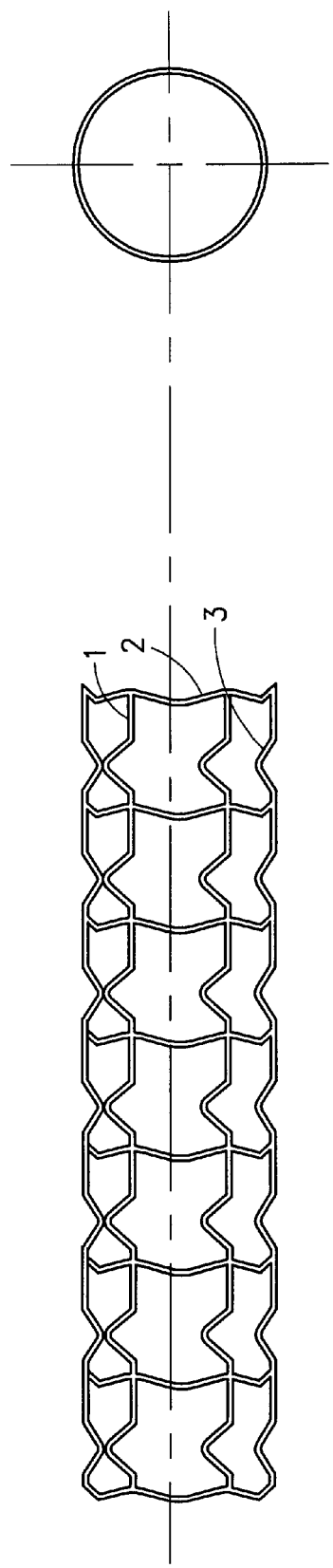
FIG. 2 shows two-dimensional diagram depicting the vascular stent.

As can be seen in FIG. 2, the vascular stent of the invention is shaped after blood vessel. Prior to implantation of the vascular stent into a narrowed blood vessel, a balloon catheter having adequate diameter and length for the vessel are inserted through the vascular stent. After implantation of the stent, the balloon is expanded for the stent to adhere to the inner surface of the vessel, which successfully restores the narrowed blood vessel to the original state and further, prevents restenosis.

Figure 3:
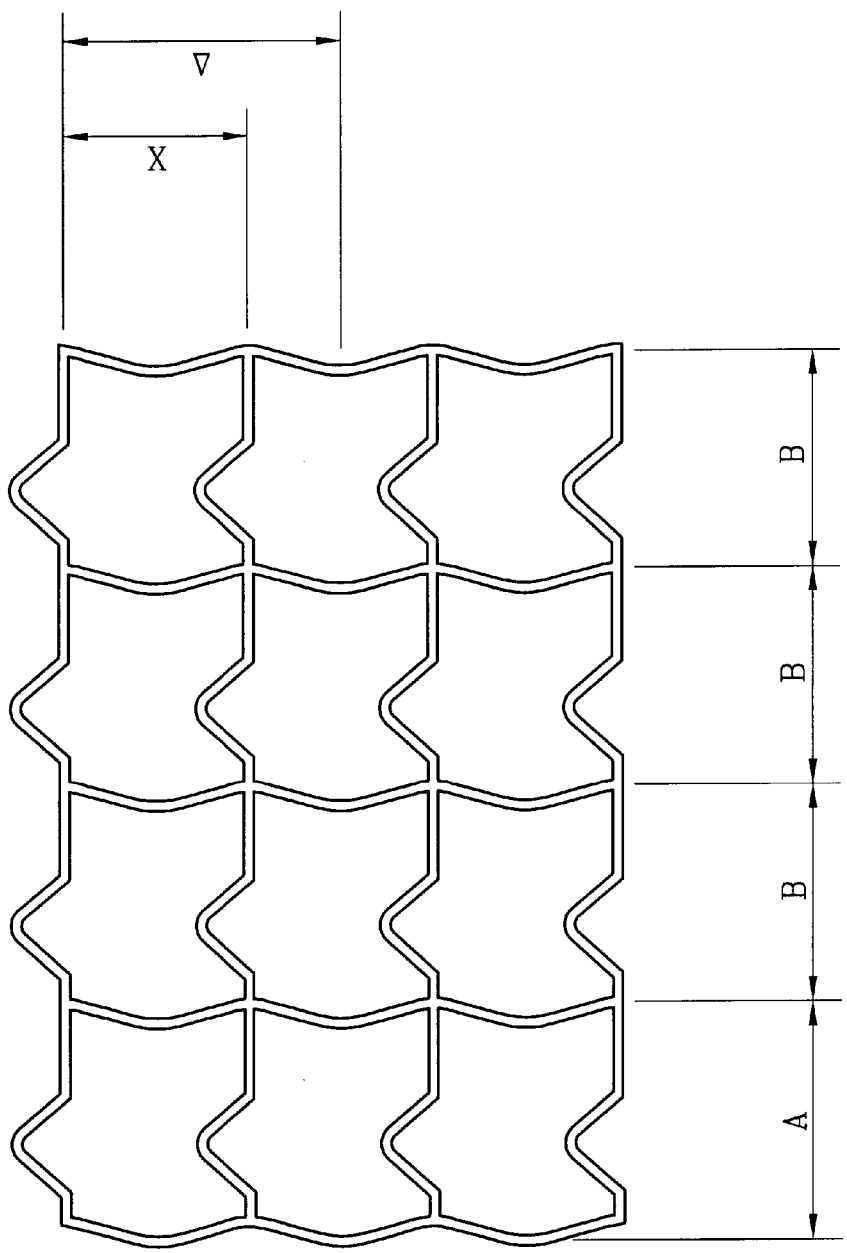
FIG. 3 is a development diagram depicting unit lengths of vertical and horizontal branches of a vascular stent as a preferred embodiment of the invention. The dimensions indicated are A=2.50 mm, B=2.25 mm, X=2.0 mm, and Δ=3.0 mm.
Figure 4:
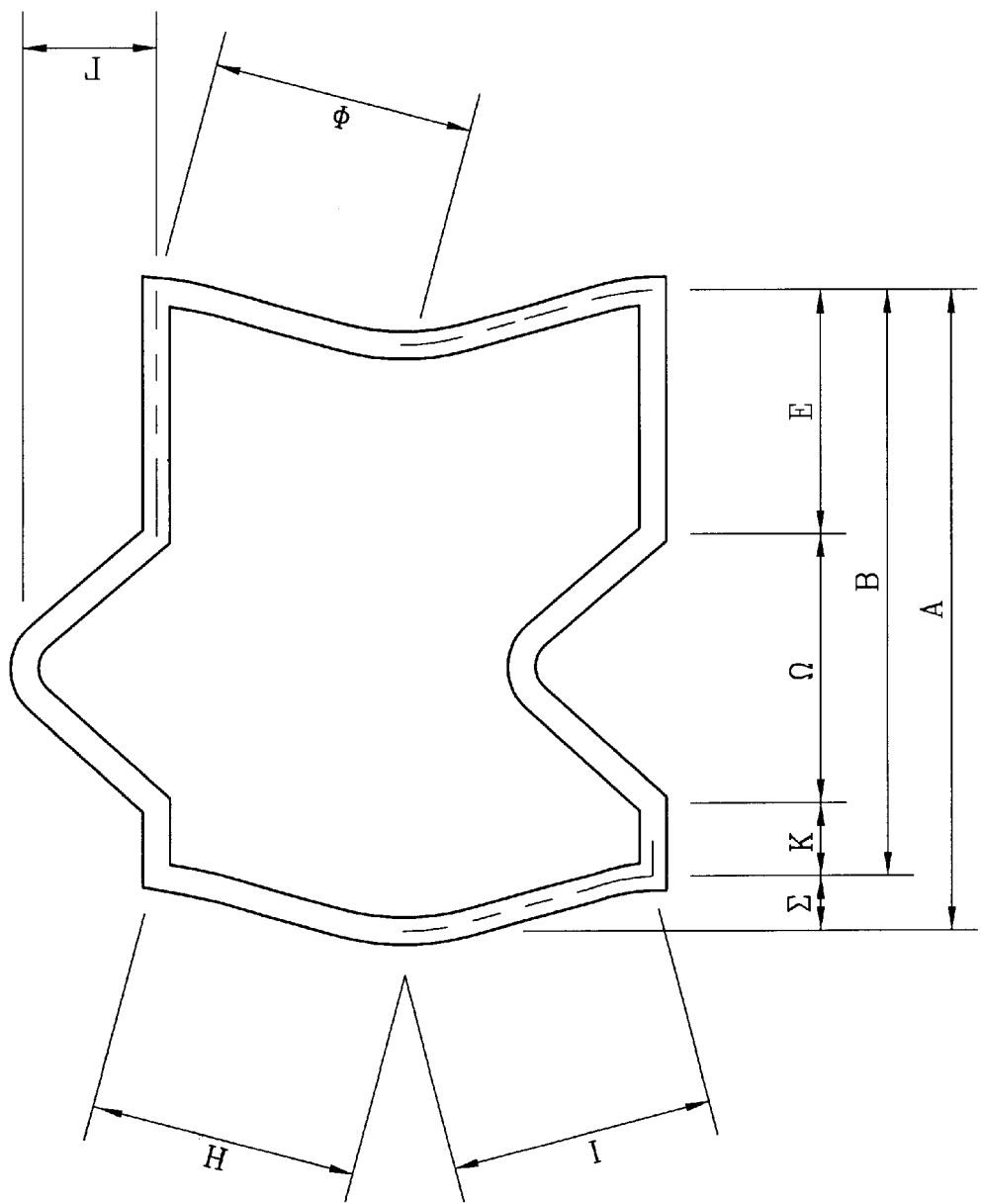
FIG. 4 is a magnification of a part of the FIG. 3, which shows a unit structure of the vascular stent. The dimensions indicated are A=2.50 mm, B=2.25 mm, Σ=0.20 mm, K=0.25 mm, Ω=1.00 mm, E=1.00 mm, I=1.0 mm, H=1.00 mm, Φ=1.00 mm, and γ=0.5 mm.
Figure 5:
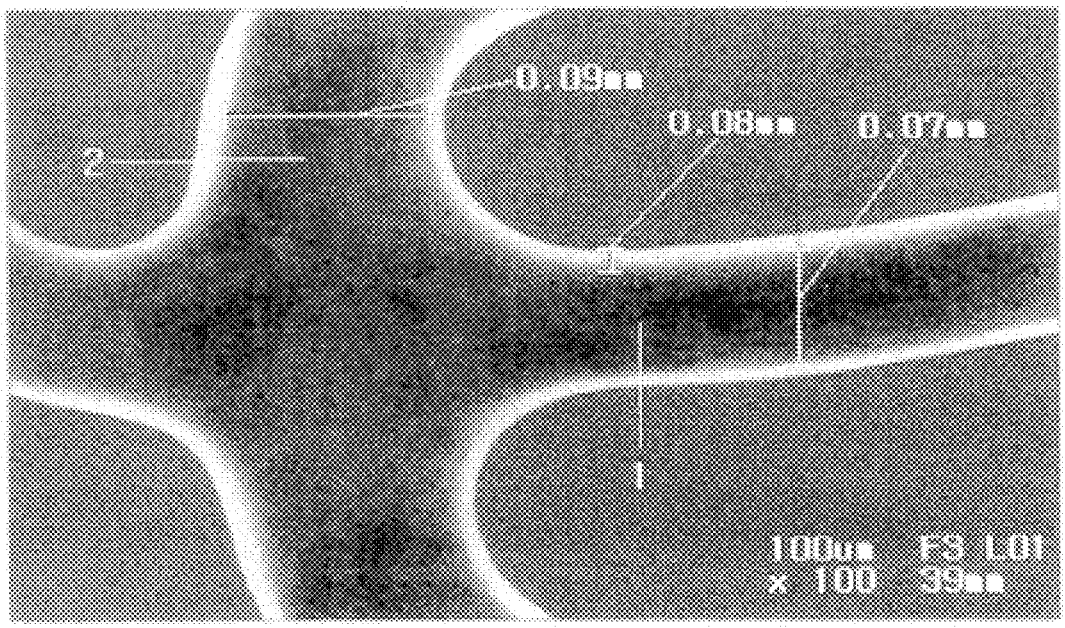
FIG. 5 is a photograph showing a magnification of a part of the finished vascular stent as a preferred embodiment of the invention.

FIG. 3 shows a vascular stent of a preferred embodiment of the invention, where the horizontal (1) and the vertical (2) branches have unit lengths of 2.25 mm and 2.0 mm, respectively. FIG. 4 is a magnification of a part of the FIG. 3, which shows a unit structure of the stent to provide more information on the structure and size of the stent. FIG. 5 is a magnification of a part of the finished stent which indicates that widths of the horizontal and vertical branches of the stent are different from each other.

As clearly illustrated as aboves, the present invention provides a vascular stent comprising wide vertical branches and narrow horizontal branches having wave-form projections, which has a vertically denser distribution. The vascular stent of the invention provides so superior flexibility as to afford excellent adaptability to the anatomy of the vessel. Moreover, the dense distribution of the branches improves strength of stability of the vascular stent, which allows the stent to sufficiently expand against high recoiling force. Implantation of the vascular stent to patients with Angina pectoris can restore the constricted blood vessels to the original state, which normalizes the blood flow rate, and further, decreases the restenosis rate as well.

While the described embodiment represents the preferred embodiment of the present invention, it is to be understood that modifications will occur to those skilled in that art without departing from the spirit of the invention. The scope of the invention is therefore to be determined solely by the appended claims.

What is claimed is:

1. A vascular stent which comprises vertical branches whose width and thickness range 0.09 to 0.12 mm and 0.08 to 0.12 mm, respectively, and horizontal branches having wave form projections, whose width and thickness range 0.05 to 0.08 mm and 0.08 to 0.12 mm, respectively.

2. The vascular stent of claim 1, wherein unit lengths of the vertical branch and the horizontal branch range 1.5 to 4.5 mm and 1.0 to 3.0 mm, respectively.

3. The vascular stent of claim 1, wherein diameter and length of the stent range 1.0 to 5.75 mm and 9.0 to 60 mm, respectively.

* * * * *